US012721826B2

(12) United States Patent
Joseph et al.

(10) Patent No.: US 12,721,826 B2
(45) Date of Patent: Sep. 1, 2026

(54) SALT OF A PHARMACEUTICAL COMPOUND

(71) Applicant: ACTIMED THERAPEUTICS LTD, Ascot (GB)

(72) Inventors: Melissa Joseph, Charlotte, NC (US); Ronnie Maxwell Lawrence, Stevenage (GB); Elaine Morten, Ascot (GB); Saurabh Chitre, Milton Bridge (GB); Natalie Louise Kelk, Milton Bridge (GB); Craig Callahan, Milton Bridge (GB)

(73) Assignee: ACTIMED THERAPEUTICS LTD, Ascot (GB)

( * ) Notice: Subject to any disclaimer, the term of this patent is extended or adjusted under 35 U.S.C. 154(b) by 0 days.

(21) Appl. No.: 19/172,147

(22) Filed: Apr. 7, 2025

(65) Prior Publication Data

US 2025/0228799 A1 Jul. 17, 2025

Related U.S. Application Data

(63) Continuation of application No. PCT/GB2024/050208, filed on Jan. 26, 2024.

(30) Foreign Application Priority Data

Jan. 27, 2023 (GB) ..................................... 2301180

(51) Int. Cl.
*A61K 31/138* (2006.01)
*A61K 47/02* (2006.01)

(52) U.S. Cl.
CPC ............ *A61K 31/138* (2013.01); *A61K 47/02* (2013.01)

(58) Field of Classification Search
CPC ..................................................... A61K 47/10
See application file for complete search history.

(56) References Cited

U.S. PATENT DOCUMENTS

| | | | | |
|---|---|---|---|---|
| 4,294,966 | A | 10/1981 | Zergenyl | |
| 4,767,784 | A * | 8/1988 | Zolss .................. | C07D 285/10 514/555 |
| 8,835,485 | B2 | 9/2014 | Springer et al. | |
| 2002/0123485 | A1* | 9/2002 | Alexander ............. | A61K 45/06 514/415 |

FOREIGN PATENT DOCUMENTS

| | | | |
|---|---|---|---|
| CH | 489466 | A | 4/1970 |
| CN | 101323580 | A | 12/2008 |
| EP | 3419610 | A1 | 1/2019 |
| WO | 2000021509 | A2 | 4/2000 |
| WO | 2008068477 | A1 | 6/2008 |
| WO | 2010125348 | A1 | 11/2010 |
| WO | 2014016585 | A1 | 1/2014 |
| WO | 2014138806 | A1 | 9/2014 |
| WO | 2014138814 | A1 | 9/2014 |
| WO | 2017144977 | A1 | 8/2017 |
| WO | 2020144146 | A1 | 7/2020 |
| WO | 2021205144 | A1 | 10/2021 |

OTHER PUBLICATIONS

International Search Report dated May 8, 2024 for corresponding International Application No. PCT/GB2024/050208, 3 pages.

* cited by examiner

*Primary Examiner* — Jared Barsky
(74) *Attorney, Agent, or Firm* — MH2 Technology Law Group, LLP

(57) ABSTRACT

The invention relates to a pharmaceutically acceptable acid addition salt of: (i) S-oxprenolol; and (ii) phosphoric acid. Medical uses of the salt and compositions comprising the salt are also described.

12 Claims, 2 Drawing Sheets

SALT OF A PHARMACEUTICAL COMPOUND

CROSS REFERENCE TO RELATED APPLICATION

This application is a continuation of International Application PCT/GB2024/050208 filed 26 Jan. 2024, the entire disclosure of which is incorporated herein by reference.

FIELD OF THE INVENTION

The present invention relates to salts of S-oxprenolol and pharmaceutical compositions comprising the salt. Medical uses of the salts are also described.

BACKGROUND OF THE INVENTION

S-oxprenolol is a β-adrenergic receptor antagonist and is also known as (−)-oxprenolol. The systematic name for S-oxprenolol is(S)-1-(2-(allyloxy) phenoxy)-3-(isopropylamino)propan-2-ol and the structure of this compound is shown below.

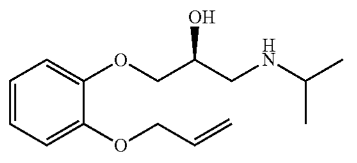 [SMILES: C=CCOc1ccccc1OC[C@@H](O)CNC(C)C]

S-oxprenolol has affinity for both beta-adrenergic receptors and 5-HT1a receptors and is useful in treating a number of disorders. WO 2014/138806 A1 describes the treatment of cachexia with S-oxprenolol and WO 2014/138814 A1 describes the treatment of amyotrophic lateral sclerosis with S-oxprenolol.

Oxprenolol is authorised for the treatment of conditions such as angina pectoris in the form of the racemate. It has been found that S-oxprenolol is the more pharmacologically active enantiomer for certain conditions. However, it is a finding of the present invention that S-oxprenolol free base has characteristics which can make it difficult to formulate as an oral medicament such as a tablet. S-oxprenolol in particular has a low melting point.

There is a need to develop a solid form of S-oxprenolol which is well-suited to use in the clinical context. In particular, it is desirable to develop a solid form of S-oxprenolol which is pharmaceutically acceptable, crystalline and has an increased melting point relative to the free base.

SUMMARY OF THE INVENTION

The inventors have found that a salt of S-oxprenolol formed with phosphoric acid is well suited to pharmaceutical formulation. In particular, this salt has been found to be crystalline and to have an increased melting point compared to S-oxprenolol free base. The salt is also pharmaceutically acceptable and has good hygroscopicity properties.

The invention provides a pharmaceutically acceptable acid addition salt of: (a) S-oxprenolol and (b) phosphoric acid.

The invention also provides a composition comprising at least 60 wt % of the pharmaceutically acceptable acid addition salt.

Further provided by the invention is a pharmaceutical composition comprising (i) the pharmaceutically acceptable acid addition salt and (ii) a pharmaceutically acceptable excipient, carrier or diluent.

The pharmaceutically acceptable acid addition salt for use in the treatment of the human or animal body is also provided by the invention.

DETAILED DESCRIPTION OF THE INVENTION

Figure 1:
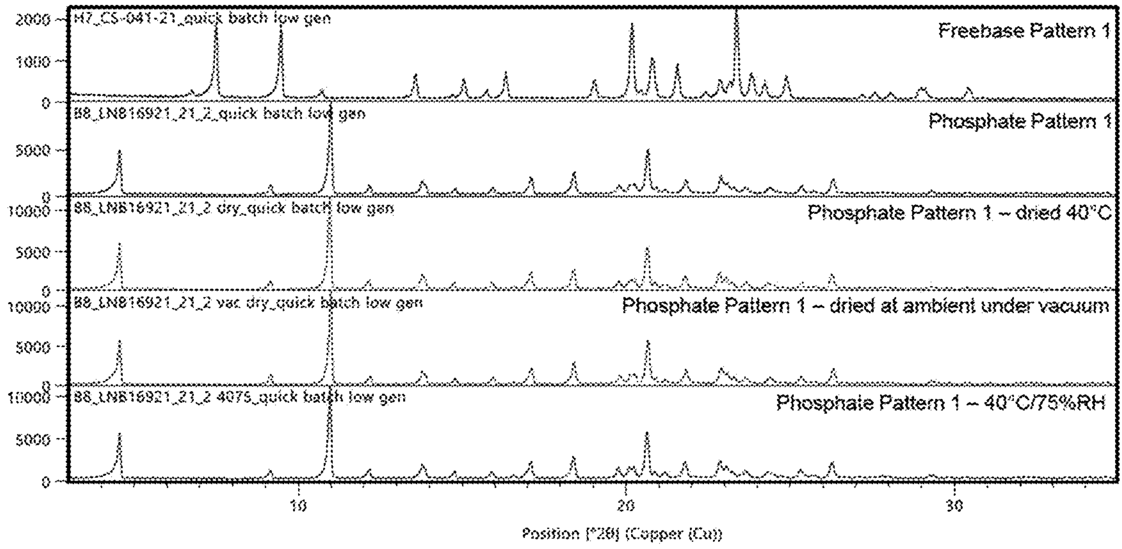
FIG. 1 shows XRPD diffractograms of S-oxprenolol free base and Pattern 1 of S-oxprenolol dihydrogenphosphate.

The pharmaceutically acceptable acid addition salt is a salt of S-oxprenolol and therefore comprises a cation formed from S-oxprenolol. The cation formed from S-oxprenolol typically has the following structure:

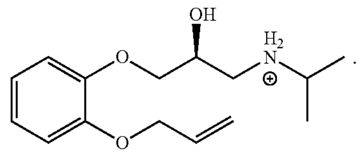

The enantiomeric excess of the S-enantiomer of the cation of oxprenolol in the pharmaceutically acceptable salt is typically at least 80% or at least 90%. The enantiomeric excess is typically at least 95%. The cation of S-oxprenolol in the pharmaceutically acceptable acid addition salt is typically substantially in the S-configuration and therefore may have an enantiomeric excess of at least 99%. Enantiomeric excess may be measured by any standard technique, for instance by measuring optical rotation or using chiral high performance liquid chromatography (HPLC).

Thus, of the cations in the salt, at least 80 mol % are typically in the S-configuration. For instance, at least 90 mol % or at least 95 mol % of the oxprenolol cations in the salt may be in the S-configuration. Preferably, at least 99 mol % of the oxprenolol cations in the salt are in the S-configuration.

The pharmaceutically acceptable acid addition salt typically does not therefore comprise greater than 10 mol % of the R-enantiomer of oxprenolol or a salt comprising a cation which is a protonated R-oxprenolol molecule. The pharmaceutically acceptable acid addition salt typically comprises less than 5.0 mol % of the R-enantiomer of oxprenolol or a salt comprising a cation which is a protonated R-oxprenolol molecule. For instance, the pharmaceutically acceptable acid addition salt is typically substantially free of the R-enantiomer of oxprenolol or a salt comprising a cation which is a protonated R-oxprenolol molecule.

The pharmaceutically acceptable acid addition salt is typically crystalline. The salt accordingly may have a three dimensional crystal structure comprising repeating unit cells. The pharmaceutically acceptable acid addition salt may be in a solid form, for instance a solid form comprising crystals or crystallites of the pharmaceutically acceptable acid addition salt.

The pharmaceutically acceptable acid salt may be in the form of a solvate. A solvate of a salt is a solid form of the salt which comprises molecules of a solvent. For instance, the salt may be a hydrate. Typically, the salt is not a solvate. For example, the pharmaceutically acceptable acid addition salt may be anhydrous.

The salt may be in the form of a hydrate, and the hydrate may comprise from 0.1 to 0.5 molecules of water per molecule of the salt (for instance about 0.25 molecules of water per molecule of the salt). The salt may be in the form of an ethanol solvate, and the ethanol solvate may comprise from 0.1 to 1.0 molecules of ethanol per molecule of the salt (for instance about 0.5 molecules of ethanol per molecule of the salt).

The pharmaceutically acceptable acid addition salt typically has a melting point which is greater than the melting point of S-oxprenolol free base. The salt may have a melting point of greater than or equal to 70° C., typically greater than or equal to 80° C. For instance, the pharmaceutically acceptable acid addition salt typically has a melting point of from 85° C. to 90° C. The melting point of the pharmaceutically acceptable acid addition salt may be about 88° C. The melting point may, for instance, be as determined using differential scanning calorimetry (DSC).

The pharmaceutically acceptable acid addition salt may comprise the cation derived from S-oxprenolol and one or more anions selected from a phosphate anion ($[PO_4]^{3-}$), hydrogenphosphate ($[HPO_4]^{2-}$) and a dihydrogenphosphate anion ($[H_2PO_4]^-$).

The pharmaceutically acceptable acid addition salt may be S-oxprenolol dihydrogenphosphate. The salt may accordingly comprise the cation derived from S-oxprenolol and a dihydrogenphosphate anion (i.e. ($[H_2PO_4]^-$). The stoichiometry of the cation and anion is typically about 1:1, for instance from 0.9:1.0 to 1.1:1.0 (i.e. for each mole of the anion, there may be from 0.9 to 1.1 moles of the cation). As such, the S-oxprenolol dihydrogenphosphate is typically S-oxprenolol mono-dihydrogen-phosphate. Accordingly, the salt may be of formula $[C_{15}H_{23}NO_3]^+[H_2PO_4]^-$, as shown below.

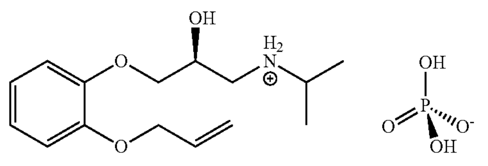

The stoichiometry of the cation and anion may alternatively be about 3:1, about 2:1 or about 1:2.

The pharmaceutically acceptable acid addition salt may be formed by any suitable method. Typically, free base S-oxprenolol is combined with the acid from which the counterion is derived (for instance phosphoric acid) in a solvent. For instance, S-oxprenolol may be dissolved in a solution of the acid in a solvent. The solvent may comprise water, an alcohol (such as methanol, ethanol, 1-propanol or isopropanol), a ketone (for instance acetone), an ester (ethyl acetate) or an ether (for instance tetrahydrofuran (THF), ethyl ether or tert-butyl methyl ether). Preferably, the solvent comprises an alcohol. The solvent may comprise at least 40 vol % of an alcohol. The solvent typically comprises ethanol.

The process for producing the pharmaceutically acceptable acid addition salt may comprise: (a) combining S-oxprenolol and phosphoric acid in a solvent comprising an alcohol to produce a solution of the pharmaceutically acceptable acid addition salt in the solvent comprising the alcohol; (b) adding a solvent comprising an alkane to the solution of the pharmaceutically acceptable acid addition salt in the solvent comprising the alcohol to produce a precipitate of the pharmaceutically acceptable acid addition salt; and (c) isolating the precipitate of the pharmaceutically acceptable acid addition salt, for instance by filtration. The process for producing the pharmaceutically acceptable acid addition salt may comprise: (a) combining S-oxprenolol and phosphoric acid in ethanol to produce a solution of the pharmaceutically acceptable acid addition salt in ethanol; (b) adding hexane or heptane to the solution of the pharmaceutically acceptable acid addition salt in ethanol to produce a precipitate of the pharmaceutically acceptable acid addition salt; and (c) isolating the precipitate of the pharmaceutically acceptable acid addition salt, for instance by filtration.

The pharmaceutically acceptable acid addition salt produced may be dissolved in the solvent or may precipitate out of solution. The pharmaceutically acceptable acid addition salt may be isolated by a suitable method, for instance by filtration or by solvent evaporation.

The pharmaceutically acceptable acid addition salt is typically crystalline. As stated herein, values of °2θ are as measured using an x-ray wavelength of Cuk α1 radiation (λ=1.54060 Å). If an x-ray powder diffraction pattern comprises a peak, the relative intensity of that peak is typically at least 5% or at least 10%. Error margins for the values of °2θ are typically ±0.2° 2θ, but the error margin may alternatively be ±0.1° 2θ.

The S-oxprenolol dihydrogenphosphate may be in the form of the crystalline polymorph of S-oxprenolol dihydrogenphosphate designated as Pattern 3. Pattern 3 of S-oxprenolol dihydrogenphosphate typically has an x-ray powder diffraction (XRPD) pattern comprising peaks at 4.8°, 7.1° and 8.2°±0.2° 2θ. The XRPD pattern may comprise peaks at 4.8°, 7.1° and 8.2°±0.1° 2θ

The XRPD pattern of S-oxprenolol dihydrogenphosphate Pattern 3 typically further comprises peaks at 22.5°, 22.7° and 23.2°±0.2° 2θ. The XRPD pattern may further comprise peaks at 22.5°, 22.7° and 23.2°±0.1° 2θ.

The XRPD pattern of S-oxprenolol dihydrogenphosphate Pattern 3 may comprise seven or more peaks selected from 4.8°, 7.1°, 8.2°, 14.2°, 14.4°, 22.5°, 22.7°, 23.2°, 23.5° and 23.8°±0.2° 2θ. The XRPD pattern may comprise all of these peaks. The error margin may be ±0.1° 2θ.

The XRPD pattern of S-oxprenolol dihydrogenphosphate Pattern 3 may comprise five or more peaks selected from 4.8°, 7.1°, 7.2°, 8.2°, 14.2°, 14.4°, 22.5°, 22.7°, 23.2°, 23.5°, 23.8° and 24.0°±0.2° 2θ. The XRPD pattern may comprise seven or more of these peaks. The XRPD pattern may comprise all of these peaks. The error margin may be ±0.1° 2θ.

The XRPD pattern of S-oxprenolol dihydrogenphosphate Pattern 3 may comprise the following peaks: 4.8°, 7.1°, 8.2°, 9.6°, 11.6°, 13.4°, 14.2°, 14.4°, 17.9°, 20.9°, 21.6°, 22.5°, 22.7°, 23.2°, 23.5°, 23.8°, 25.0°, 25.8° and 27.0°±0.2° 2θ. The error margin may be ±0.1° 2θ.

The XRPD pattern of S-oxprenolol dihydrogenphosphate Pattern 3 may comprise the following peaks.

| S-oxprenolol dihydrogenphosphate Pattern 3 | |
|---|---|
| Pos. [°2θ] | Rel. Int. [%] |
| 4.8 | 100.0 |
| 7.1 | 49.6 |
| 7.2 | 20.9 |
| 8.2 | 28.7 |
| 9.6 | 11.9 |
| 11.6 | 12.9 |
| 13.4 | 11.7 |
| 14.2 | 17.8 |
| 14.4 | 16.2 |
| 18.0 | 12.4 |
| 20.9 | 11.8 |
| 21.6 | 13.2 |
| 22.5 | 31.2 |
| 22.7 | 53.9 |
| 23.2 | 31.5 |
| 23.5 | 34.3 |
| 23.8 | 17.8 |
| 24.0 | 15.7 |
| 25.0 | 12.5 |
| 25.8 | 10.4 |
| 27.0 | 10.9 |

Figure 4:
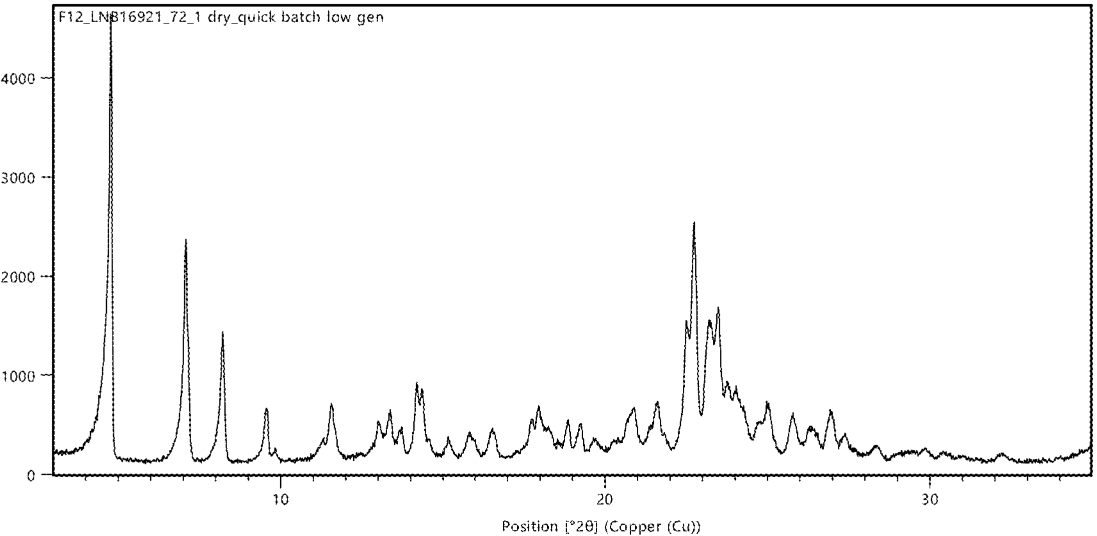
FIG. 4 shows an XRPD diffractograms of Pattern 3 of S-oxprenolol dihydrogenphosphate.

The XRPD pattern of S-oxprenolol dihydrogenphosphate Pattern 3 may be substantially as shown in FIG. 4.

S-oxprenolol dihydrogenphosphate Pattern 3 may have the following unit cell parameters (as determined by single crystal analysis).

Orthorhombic $P2_1$ a=7.76070(10) Å α=90° b=36.7729(6) Å β=94.0602(11)° C.

c=12.9496(2) Å γ=90°

Volume=3686.33(10) $Å^3$

Z=8, Z`=4

Temperature=100 K

The infrared spectrum of S-oxprenolol dihydrogenphosphate Pattern 3 typically comprises peaks at about 1210 to 1260 $cm^{-1}$ (C—O—C functional group) and at about 1590 $cm^{-1}$ (N—H bending).

The melting point of S-oxprenolol dihydrogenphosphate Pattern 3 is typically in the range of 85.0 to 90.0° C., for instance about 88° C. The melting point may be as measured by DSC analysis.

S-oxprenolol dihydrogenphosphate Pattern 3 may be produced by a process comprising recrystallizing S-oxprenolol dihydrogenphosphate from a solvent which is ethanol, isopropanol, acetone, a mixture of acetone and water, diisopropyl ether, n-heptane, n-hexane, methanol, methyl isobutyl ketone, tert-butyl methyl ether, tetrahydrofuran or toluene. Typically, the solvent for the recrystallization contains at least 90% by volume of the stated solvent component.

S-oxprenolol dihydrogenphosphate Pattern 3 may be obtainable by addition of a THF anti-solvent into a 90% acetone: 10% water solution of S-oxprenolol dihydrogenphosphate and storing the resulting mixture at 25° C. for two weeks.

S-oxprenolol dihydrogenphosphate Pattern 3 is typically a hydrate and the unit cell typically comprises about 0.25 molecules of water per molecule of S-oxprenolol dihydrogenphosphate.

The S-oxprenolol dihydrogenphosphate may be in the form of the crystalline polymorph of S-oxprenolol dihydrogenphosphate designated as Pattern 2. Pattern 2 of S-oxprenolol dihydrogenphosphate typically has an x-ray powder diffraction (XRPD) pattern comprising peaks at 6.8°, 7.8° and 22.5°±0.2° 2θ. The XRPD pattern may comprise peaks at 6.8°, 7.8° and 22.5°±0.1° 2θ.

The XRPD pattern of S-oxprenolol dihydrogenphosphate Pattern 2 typically further comprises peaks at 4.4°, 17.0° and 22.6°±0.2° 2θ. The XRPD pattern may further comprise peaks at 4.4°, 17.0° and 22.6°±0.1° 2θ.

The XRPD pattern of S-oxprenolol dihydrogenphosphate Pattern 2 may comprise peaks at 4.4°, 6.8°, 7.8°, 17.0° and 22.5°±0.2° 2θ. The error margin may be ±0.1° 2θ.

The XRPD pattern of S-oxprenolol dihydrogenphosphate Pattern 2 may comprise seven or more peaks selected from 4.4°, 6.8°, 7.8°, 17.0°, 22.5°, 22.9°, 23.5°, 23.6°, 24.2° and 25.1°±0.2° 2θ. The XRPD pattern may comprise all of these peaks. The error margin may be ±0.1° 2θ.

The XRPD pattern of S-oxprenolol dihydrogenphosphate Pattern 2 may comprise five or more peaks selected from 4.4°, 6.8°, 7.8°, 17.0°, 22.5°, 22.6°, 22.9°, 23.5°, 23.6°, 24.2° and 25.1°±0.2° 2θ. The XRPD pattern may comprise seven or more of these peaks. The XRPD pattern may comprise all of these peaks. The error margin may be ±0.1° 2θ.

The XRPD pattern of S-oxprenolol dihydrogenphosphate Pattern 2 may comprise the following peaks: 4.4°, 6.8°, 7.8°, 13.0°, 17.0°, 17.2°, 19.3°, 21.9°, 22.5°, 22.9°, 23.5°, 23.6°, 24.2° and 25.1°±0.2° 2θ. The error margin may be ±0.1° 2θ.

The XRPD pattern of S-oxprenolol dihydrogenphosphate Pattern 2 may comprise the following peaks.

| S-oxprenolol dihydrogenphosphate Pattern 2 | |
|---|---|
| Pos. [°2θ] | Rel. Int. [%] |
| 4.1 | 14.4 |
| 4.4 | 52.5 |
| 6.8 | 97.4 |
| 7.8 | 35.0 |
| 12.9 | 21.0 |
| 13.7 | 13.7 |
| 17.0 | 23.0 |
| 17.2 | 21.1 |
| 19.3 | 20.0 |
| 21.9 | 11.1 |
| 22.5 | 100.0 |
| 22.6 | 79.6 |
| 22.9 | 23.8 |
| 23.5 | 96.1 |
| 23.6 | 61.2 |
| 24.2 | 23.3 |
| 25.1 | 21.3 |

Figure 3:
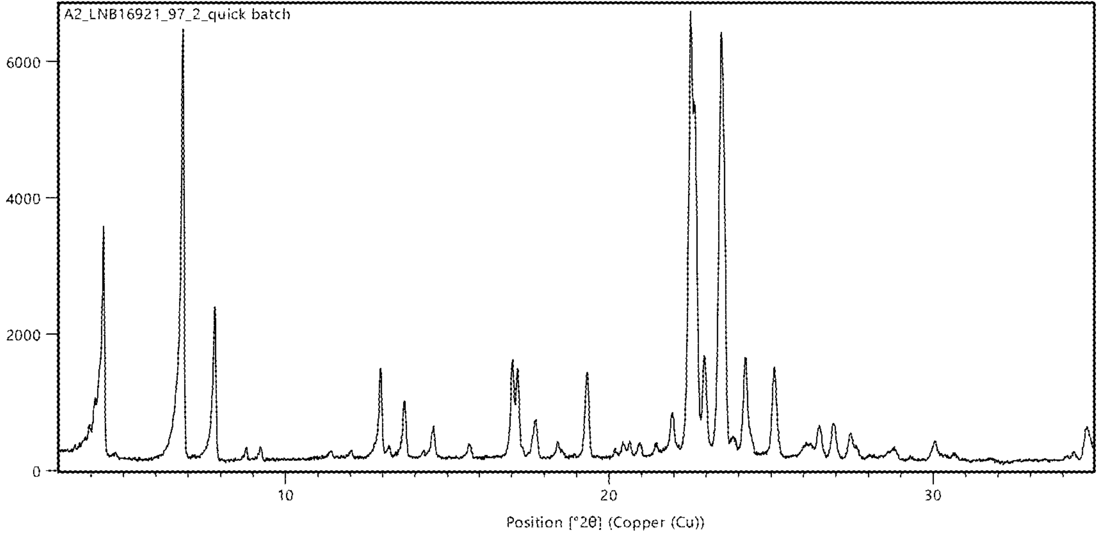
FIG. 3 shows an XRPD diffractograms of Pattern 2 of S-oxprenolol dihydrogenphosphate.

The XRPD pattern of S-oxprenolol dihydrogenphosphate Pattern 2 may be substantially as shown in FIG. 3.

S-oxprenolol dihydrogenphosphate Pattern 2 may have the following unit cell parameters (as determined by single crystal analysis).

Orthorhombic $P2_12_12_1$ a=7.7822(4) Å α=90° b=13.2653(5) Å β=90° C.

c=39.5732(15) Å γ=90°

Volume=4085.3(3) $Å^3$

Z=4, Z`=2

Temperature=100(2) K

S-oxprenolol dihydrogenphosphate Pattern 2 may be produced by a process comprising recrystallizing S-oxprenolol dihydrogenphosphate from a solvent which is 1-propanol, 2-methyl-1-propanol, acetonitrile, anisole, benzyl alcohol, butyl acetate, isopropyl acetate or methyl ethyl ketone.

S-oxprenolol dihydrogenphosphate Pattern 2 is typically an ethanol solvate and the unit cell typically comprises about 0.5 molecules of ethanol per molecule of S-oxprenolol dihydrogenphosphate.

The S-oxprenolol dihydrogenphosphate may be in the form of the crystalline polymorph of S-oxprenolol dihydrogenphosphate designated as Pattern 1. Pattern 1 of S-oxprenolol dihydrogenphosphate typically has an x-ray powder diffraction (XRPD) pattern comprising peaks at 4.6°, 11.0° and 20.6°±0.2° 2θ. The XRPD pattern may comprise peaks at 4.6°, 11.0° and 20.6°±0.1° 2θ.

The XRPD pattern of S-oxprenolol dihydrogenphosphate Pattern 1 typically further comprises peaks at 17.1°, 18.4° and 22.9°±0.2° 2θ. The XRPD pattern may further comprise peaks at 17.1°, 18.4° and 22.9°±0.1° 2θ.

The XRPD pattern of S-oxprenolol dihydrogenphosphate Pattern 1 may comprise five or more peaks selected from 4.6°, 11.0°, 13.8°, 17.1°, 18.4°, 20.6°, 21.8°, 22.9° and 26.3°±0.2° 2θ. The XRPD pattern may comprise seven or more of these peaks. The XRPD pattern may comprise all of these peaks. The error margin may be ±0.1° 2θ.

The XRPD pattern of S-oxprenolol dihydrogenphosphate Pattern 1 may comprise the following peaks.

S-oxprenolol dihydrogenphosphate Pattern 1

| Pos. [°2θ] | Rel. Int. [%] |
|---|---|
| 4.6 | 48.9 |
| 11.0 | 100.0 |
| 12.2 | 10.3 |
| 13.8 | 15.2 |
| 17.1 | 18.3 |
| 18.4 | 22.6 |
| 20.1 | 10.5 |
| 20.3 | 11.1 |
| 20.6 | 46.6 |
| 21.8 | 15.1 |
| 22.9 | 18.8 |
| 23.0 | 12.2 |
| 26.3 | 16.3 |

The XRPD pattern of S-oxprenolol dihydrogenphosphate Pattern 1 may be substantially as shown in FIG. 1.

Also provided is S-oxprenolol dihydrogenphosphate, wherein the S-oxprenolol dihydrogenphosphate is characterised by an XRPD pattern comprising peaks at 4.8°, 7.1° and 8.2°±0.2° 2θ. The XRPD pattern may further comprises peaks at 22.5°, 22.7° and 23.2°±0.2° 2θ. The XRPD may comprise seven or more peaks selected from 4.8°, 7.1°, 8.2°, 14.2°, 14.4°, 22.5°, 22.7°, 23.2°, 23.5° and 23.8°±0.2° 2θ. The error margin may be ±0.1° 2θ.

Also provided is S-oxprenolol dihydrogenphosphate, wherein the S-oxprenolol dihydrogenphosphate is characterised by an x-ray powder diffraction pattern comprising peaks at 6.8°, 7.8° and 22.5°±0.2° 2θ. The XRPD pattern may comprise peaks at 4.4°, 6.8°, 7.8°, 17.0° and 22.5°±0.2° 2θ. The XRPD pattern may comprise seven or more peaks selected from 4.4°, 6.8°, 7.8°, 17.0°, 22.5°, 22.9°, 23.5°, 23.6°, 24.2° and 25.1°±0.2° 2θ. The error margin may be ±0.1° 2θ.

Also provided is S-oxprenolol dihydrogenphosphate, wherein the S-oxprenolol dihydrogenphosphate is characterised by an x-ray powder diffraction pattern comprising peaks at 4.6°, 11.0° and 20.6°±0.2° 2θ. The XRPD pattern may further comprise peaks at 17.1°, 18.4° and 22.9°±0.2° 2θ. The XRPD pattern may comprise five or more peaks selected from 4.6°, 11.0°, 13.8°, 17.1°, 18.4°, 20.6°, 21.8°, 22.9° and 26.3°±0.2° 2θ. The error margin may be ±0.1° 2θ.

The invention further provides a pharmaceutically acceptable acid addition salt of (i) S-oxprenolol and (ii) an acid selected from oxalic acid, 1-hydroxy-2-naphthoic acid (xinafoic acid), hippuric acid (N-benzoylglycine), acetic acid and naphthalene-1,5-disulfonic acid. The pharmaceutically acceptable acid addition salt formed from these acids may be as described above for the salt formed with phosphoric acid.

The pharmaceutically acceptable acid addition salt may be of (i) S-oxprenolol and (ii) oxalic acid, i.e. S-oxprenolol oxalate. The pharmaceutically acceptable acid addition salt may be S-oxprenolol hemi-oxalate ($[C_{15}H_{23}NO_3]_2^+$ $[O_2CCO_2]^{2-}$) or S-oxprenolol mono-oxalate ($[C_{15}H_{23}NO_3]^+$ $[HO_2CCO_2]^-$). The salt is typically S-oxprenolol mono-oxalate (i.e. S-oxprenolol hydrogenoxalate).

The pharmaceutically acceptable acid addition salt of (i) S-oxprenolol and (ii) oxalic acid is typically crystalline. The S-oxprenolol oxalate may be in the form of the crystalline polymorph of S-oxprenolol oxalate designated as Pattern 1. Pattern 1 of S-oxprenolol oxalate typically has an x-ray powder diffraction (XRPD) pattern comprising peaks at 10.7°, 15.5° and 24.7°±0.2° 2θ. The XRPD pattern may comprise peaks at 10.7°, 15.5° and 24.7°±0.1° 2θ.

The XRPD pattern of S-oxprenolol oxalate Pattern 1 typically further comprises peaks at 7.7°, 8.8° and 17.0°±0.2° 2θ. The XRPD pattern may further comprise peaks at 7.7°, 8.8° and 17.0°±0.1° 2θ.

The XRPD pattern of S-oxprenolol oxalate Pattern 1 may comprise five or more peaks selected from 7.7°, 8.8°, 10.7°, 15.5°, 17.0°, 17.4°, 17.7°, 18.7°, 19.7°, 20.3°, 22.9°, 23.3°, 24.3°, 24.7°, 25.6° and 26.3°±0.2° 2θ. The XRPD pattern may comprise seven or more of these peaks. The error margin may be ±0.1° 2θ.

The XRPD pattern may comprise all of these peaks. The XRPD pattern of S-oxprenolol oxalate Pattern 1 may comprise the following peaks.

S-oxprenolol oxalate Pattern 1

| Pos. [°2θ] | Rel. Int. [%] |
|---|---|
| 27.0 | 12.6 |
| 26.3 | 16.9 |
| 25.6 | 33.9 |
| 25.6 | 37.8 |
| 25.3 | 13.8 |
| 24.7 | 62.4 |
| 24.3 | 30.5 |
| 24.3 | 31.5 |
| 23.3 | 17.4 |
| 22.9 | 38.6 |
| 21.4 | 11.2 |
| 20.3 | 25.5 |
| 19.7 | 21.4 |
| 18.7 | 17.9 |
| 17.7 | 15.5 |
| 17.4 | 16.6 |
| 17.0 | 40.4 |
| 15.5 | 61.2 |
| 10.7 | 100.0 |
| 8.8 | 52.6 |
| 7.7 | 40.4 |

The S-oxprenolol oxalate may be in the form of the crystalline polymorph of S-oxprenolol oxalate designated as Pattern 2. Pattern 2 of S-oxprenolol oxalate typically has an x-ray powder diffraction (XRPD) pattern comprising peaks at 9.0°, 22.5° and 24.4°±0.2° 2θ. The XRPD pattern may comprise peaks at 9.0°, 22.5° and 24.4°±0.1° 2θ.

The XRPD pattern of S-oxprenolol oxalate Pattern 2 typically further comprises peaks at 8.8°, 18.0° and 23.3°±0.2° 2θ. The XRPD pattern may further comprise peaks at 8.8°, 18.0° and 23.3°±0.1° 2θ.

The XRPD pattern of S-oxprenolol oxalate Pattern 2 may comprise five or more peaks selected from 8.8°, 9.0°, 18.0°, 18.2°, 18.8°, 20.6°, 22.5°, 23.3°, 23.6°, 24.4° and 24.9°±0.2° 2θ. The XRPD pattern may comprise seven or more of these peaks. The XRPD pattern may comprise all of these peaks. The error margin may be ±0.1° 2θ.

The XRPD pattern of S-oxprenolol oxalate Pattern 2 may comprise the following peaks.

| S-oxprenolol oxalate Pattern 2 | |
|---|---|
| Pos. [°2θ] | Rel. Int. [%] |
| 8.8 | 24.6 |
| 9.0 | 100.0 |
| 18.0 | 14.5 |
| 18.2 | 7.9 |
| 18.8 | 11.6 |
| 20.6 | 5.8 |
| 22.5 | 29.5 |
| 23.3 | 14.2 |
| 23.6 | 6.1 |
| 24.4 | 46.4 |
| 24.9 | 10.6 |

Also provided is S-oxprenolol oxalate characterised by an XRPD pattern comprising peaks at 10.7°, 15.5° and 24.7°±0.2° 2θ. The XRPD pattern may further comprise peaks at 7.7°, 8.8° and 17.0°±0.2° 2θ. The XRPD pattern may comprise five or more peaks selected from 7.7°, 8.8°, 10.7°, 15.5°, 17.0°, 17.4°, 17.7°, 18.7°, 19.7°, 20.3°, 22.9°, 23.3°, 24.3°, 24.7°, 25.6° and 26.3°±0.2° 2θ. The error margin may be ±0.1° 2θ.

Also provided is S-oxprenolol oxalate characterised by an XRPD pattern comprising peaks at 9.0°, 22.5° and 24.4°±0.2° 2θ. The XRPD pattern may further comprise peaks at 8.8°, 18.0° and 23.3°±0.2° 2θ. The XRPD pattern may comprise five or more peaks selected from 8.8°, 9.0°, 18.0°, 18.2°, 18.8°, 20.6°, 22.5°, 23.3°, 23.6°, 24.4° and 24.9°±0.2° 2θ. The error margin may be ±0.1° 2θ.

Composition

The composition provided by the invention comprises at least 60 wt % of the pharmaceutically acceptable acid addition salt. The composition may comprise at least 80 wt % or at least 95 wt % of the pharmaceutically acceptable acid addition salt relative to the total weight of the composition. The composition may consist essentially of the pharmaceutically acceptable acid addition salt. The composition may consist of the pharmaceutically acceptable acid addition salt.

The composition accordingly typically comprises no more than 30 wt % of R-oxprenolol or a salt thereof relative to the total weight of the composition. For instance, the composition may comprise no more than 10 wt %, or no more than 1 wt %, of R-oxprenolol or a salt thereof relative to the total weight of the composition.

The pharmaceutical composition of the invention comprises (i) the pharmaceutically acceptable acid addition salt and (ii) a pharmaceutically acceptable excipient, carrier or diluent. The pharmaceutical composition may, for instance, be: a tablet, capsule, powder, solution or suspension for oral administration; a solution or suspension for injection; or a solution, suspension or powder for inhalation. The pharmaceutical composition is typically a tablet.

The pharmaceutical composition is typically substantially free of R-oxprenolol or a salt thereof. For instance, the pharmaceutical composition may comprise less than 1.0 wt %, or less than 0.5 wt %, of R-oxprenolol or a salt thereof. The enantiomeric excess of the S-oxprenolol salt in the pharmaceutical composition is typically at least 80%, at least 90%, at least 95% or at least 99%.

Pharmaceutically acceptable excipients, carriers and diluents are well known to the skilled person.

The diluent may be any pharmaceutically acceptable diluent. The diluent is typically suitable for parenteral administration or for oral administration. Examples of suitable liquid diluents include water, ethanol and glycerol. The diluent may alternatively be selected from solid diluents such as lactose, dextrose, saccharose, cellulose, corn starch and potato starch. The diluent may contain buffer components to control the pH. The buffers may be derived from phosphate, citrate or acetate. The diluent may also contain sodium chloride.

The pharmaceutical composition may comprise an excipient selected from: lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tableting, sugar coating, or film coating processes.

The pharmaceutical composition may for instance be a tablet comprising one or more excipients selected from magnesium stearate, colloidal silica, microcrystalline cellulose, strearyl fumarate and starch.

Compositions which are liquid dispersions for oral administration may be syrups, emulsions and suspensions. The syrups may contain as carriers, for example, saccharose, glycerine, mannitol or sorbitol.

Compositions which are suspensions or emulsions may contain as carrier, for example a natural gum, agar, sodium alginate, pectin, methylcellulose, carboxymethylcellulose, or polyvinyl alcohol. The suspension or solutions for intramuscular injections may contain, together with the pharmaceutically acceptable acid addition sat, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion, or for inhalation, may contain as carrier, for example, sterile water or they may be in the form of sterile, aqueous, isotonic saline solutions.

The pharmaceutical composition may comprise the pharmaceutically acceptable acid addition salt in an amount equivalent to from 0.1 to 1000 mg of S-oxprenolol free base. For instance, the pharmaceutical composition may comprise the pharmaceutically acceptable acid addition salt in an amount equivalent to from 20 to 400 mg or from 100 to 300 mg of S-oxprenolol free base. For example, 134 mg of S-oxprenolol dihydrogenphosphate (molecular weight 363.3 $gmol^{-1}$) is equivalent to 100 mg S-oxprenolol free base (molecular weight 265.3 $gmol^{-1}$).

Medical Uses

The pharmaceutically acceptable acid addition salt is useful in the treatment or prevention of a disease or condition selected from cachexia, sarcopenia, a neuromuscular disorder, muscle weakness, hypertension, heart failure, atrial fibrillation, heart attack, angina pectoris, glaucoma and anxiety. Typically the disease or condition is selected from cachexia, a neuromuscular disorder and muscle weakness.

The cachexia may be caused by an underlying condition. For instance, the cachexia may be caused by cancer, heart failure, chronic obstructive pulmonary diseases (COPD), liver failure, kidney failure, stroke, rheumatoid arthritis, severe burn injury or HIV/AIDS. The muscle weakness may be caused by an underlying condition. For instance, the muscle weakness may be caused by trauma, musculoskeletal injury, surgery or immobilization. The muscle weakness may be intensive care unit acquired weakness (ICUAW). The neuromuscular disorder may for instance be amyotrophic lateral sclerosis (ALS).

The invention also provides a method of treating or preventing a disease or condition selected from cachexia, sarcopenia, a neuromuscular disorder, muscle weakness, hypertension, heart failure, atrial fibrillation, heart attack, angina pectoris, glaucoma and anxiety in an individual, the method comprising administering a therapeutically effective amount of the pharmaceutically acceptable acid addition salt to the individual.

The pharmaceutically acceptable acid addition salt is typically administered orally or parenterally.

An effective amount of the pharmaceutically acceptable acid addition salt is typically an amount equivalent to from 0.1 to 1000 mg of S-oxprenolol free base for a single dose. For instance, a single dose of the pharmaceutically acceptable acid addition salt may be a dose equivalent to from 20 to 400 mg or from 100 to 300 mg of S-oxprenolol free base. The dose may be administered once, twice or three times a day, for instance two or three times a day. For example, the total daily dose of the pharmaceutically acceptable acid addition salt may be a dose equivalent to from 300 to 800 mg of S-oxprenolol free base.

The following Examples illustrate the invention.

EXAMPLES

Methods of Analysis

X-Ray Powder Diffraction (XRPD)

XRPD analysis was carried out on a PANalytical X'pert pro with PIXcel detector (128 channels), scanning the samples between 3 and 35° 2θ. The material was gently ground to release any agglomerates and loaded onto a multi-well plate with Kapton or Mylar polymer film to support the sample. The multi-well plate was then placed into the diffractometer and analysed using Cu K radiation ($\alpha1$ $\lambda$=1.54060 Å; $\alpha2$=1.54443 Å; $\beta$=1.39225 Å; $\alpha1$: $\alpha2$ ratio=0.5) running in transmission mode (step size 0.0130° 2θ, step time 18.87s) using 40 kV/40 mA generator settings. Data were visualized and images generated using the HighScore Plus 4.7 desktop application (PANalytical, 2017).

Polarised Light Microscopy (PLM)

The presence of crystallinity (birefringence) was determined using an Olympus BX50 microscope, equipped with cross-polarising lenses and a Motic camera. Images were captured using Motic Images Plus 3.0. All images were recorded using the 20× objective, unless otherwise stated.

Thermogravimetric Analysis/Differential Scanning Calorimetry (TGA/DSC)

Approximately 5 mg of material was added into a pretared open aluminum pan and loaded into a TA Instruments Discovery SDT 650 Auto-Simultaneous DSC and held at room temperature. The sample was then heated at a rate of 10° C./min from 30° C. to 400° C. during which time the change in sample weight was recorded along with the heat flow response (DSC). Nitrogen was used as the sample purge gas, at a flow rate of 200 cm$^3$/min.

Example 1—Characterisation of S-oxprenolol

A solid sample of S-oxprenolol was analysed by XRPD and TGA/DSC.

S-oxprenolol was determined to be crystalline by XRPD, with small, birefringent particles observed by PLM. Aggregation of the material was observed in the PLM, with a mixture of small and large aggregates noted along with the small discrete rod-like particles.

Thermal analysis of the material indicated there was an endothermic event in the DSC at an onset temperature of 56° C., with a peak at 59° C. No further thermal events were observed in the DSC during further heating or cooling of the sample. TGA showed no significant weight losses prior to decomposition, with decomposition of the material above 150° C.

Due to the low melting point observed during the thermal analysis of the molecule, additional development was conducted to identify a solid form with more favourable physical properties such as a higher melting point.

Example 2—Initial Salt Screening of S-oxprenolol

A salt screen was conducted for S-oxprenolol using 31 counterions and 6 solvent systems. The acids from which the counterions were derived are shown in Table 1 and the solvent systems are shown in Table 2.

TABLE 1

| Acid | Molecular Wt. (g/mol) | $pKa_1$ | $pKa_2$ | $pKa_3$ |
|---|---|---|---|---|
| Hydrochloric acid | 36.46 | −6 | | |
| Sulfuric acid | 98.08 | −3 | 1.9 | |
| Benzenesulfonic acid | 158.18 | 0.7 | | |
| L-Aspartic acid | 133.11 | 1.9 | 3.7 | |
| Maleic acid | 116.08 | 1.9 | 6.2 | |
| Phosphoric acid | 98 | 2 | 7.1 | 12 |
| L-Tartaric acid | 150.09 | 3 | 4.4 | |
| Fumaric acid | 116.08 | 3 | 4.4 | |
| Citric acid | 192.13 | 3.1 | 4.8 | 6.4 |
| D-Gluconic acid | 196.16 | 3.8 | | |
| Succinic acid | 118.09 | 4.2 | 5.6 | |
| Benzoic acid | 122.12 | 4.2 | | |
| DL-Lactic acid | 90.08 | 3.9 | | |
| 1-Hydroxy-2-naphthoic acid | 188.17 | 2.7 | 13.5 | |
| Acetic acid | 60.05 | 4.8 | | |
| L-Ascorbic acid | 176.13 | 4.2 | 11.6 | |
| Camphorsulfonic acid | 232.29 | 2.2 | | |
| Ethanesulfonic acid | 110.13 | 2.1 | | |
| Gentisic acid | 154.12 | 2.9 | | |
| Hippuric acid | 179.17 | 3.6 | | |
| Methanesulfonic acid | 96.1 | −1.2 | | |
| Oxalic acid | 90.04 | 1.3 | 4.3 | |
| Pamoic acid | 388.37 | 2.5 | 3.1 | |
| Salicylic acid | 138.12 | 3 | 13.8 | |
| Toluenesulfonic acid | 190.22 | −1.3 | | |
| Adipic acid | 146.14 | 4.44 | 5.44 | |
| Ethane-1,2-disulfonic acid | 190.2 | −2.1 | −1.5 | |
| Glutaric acid | 132.11 | 4.34 | | |
| Malonic acid | 104.06 | 2.83 | 5.7 | |
| Naphthalene-1,5-disulfonic acid | 288.3 | −3.4 | −2.6 | |
| Phthalic acid | 166.13 | 2.89 | 5.51 | |

TABLE 2

| Solvent | Free base Solubility (mg/mL) |
|---|---|
| Acetone | >195 |
| Ethanol | >196 |
| Ethyl Acetate | >197 |
| tert-Butylmethyl Ether | >207* |
| Tetrahydrofuran | >196 |
| Water | <10 |

*dissolved at 40° C.

The salt screen was conducted as follows. To ca. 25 mg of S-oxprenolol free base in 1.5 mL screw cap vials, 100 μL of the appropriate solvent system was added to create a solution. For the water experiments 300 μL was added to create slurries. 1.05 equivalents of counterion was weighed into separate 1.5 mL screw cap vials. A slurry/solution of the counterion in 100-300 μL of the appropriate solvent was added to the free base solution/slurry. For liquid counterions a stock solution was prepared in the allocated solvent and added to the S-oxprenolol solution/slurry. For HCl a stock solution was prepared in ethanol and used for the t-BME experiment for miscibility. For the D-gluconic acid experiments water was used for the D-gluconic acid stock for miscibility.

Temperature cycling was carried out between ambient temperature (ca. 20° C.) and 40° C. in 4 hour cycles for ca. 3 days. Hold periods of 4 h at ambient temperature (ca. 20° C.) and 4 h hold periods at 40° C. were carried out. After temperature cycling, slurries were isolated by centrifuge filtration (nylon, 0.22 μm) and analyzed by XRPD.

Solutions were allowed to evaporate at ambient temperature (ca. 20° C.) and pressure. Potential salts were dried at 40° C. under vacuum for ca. 19 h and re-analyzed by XRPD then stored at 40° C./75% RH for ca. 19 h and re-analyzed by XRPD.

Of the counterions tested, the majority did not form solid crystalline salts with S-oxprenolol. Most counterions formed a gum or oil with S-oxprenolol. The results are shown in Table 3.

TABLE 3

| | Solvent | | | | | |
|---|---|---|---|---|---|---|
| Counterion | acetone | ethanol | ethyl acetate | t-BME | THF | water |
| hydrochloric acid | oil | oil | oil | oil | oil | oil |
| sulfuric acid | oil | oil | oil | oil | oil | oil |
| benzenesulfonic acid | oil | oil | oil | oil | oil | oil |
| l-aspartic acid | counterion | counterion | counterion | counterion | counterion | counterion |
| maleic acid | oil | oil | oil | oil | oil | oil |
| phosphoric acid | gum | crystalline salt | gum | gum | oil | oil |
| l-tartaric acid | oil | oil | gum | counterion | oil | oil |
| fumaric acid | gum | gum | gum | gum | gum | counterion |
| citric acid | gum | oil | gum | gum | gum | oil |
| d-gluconic acid | oil | oil | oil | oil | oil | oil |
| succinic acid | oil | oil | oil | gum | oil | oil |
| benzoic acid | oil | oil | oil | oil | oil | oil |
| dl-lactic acid | oil | oil | oil | oil | oil | oil |
| 1-hydroxy-2-naphthoic acid | gum | crystalline salt | crystalline salt | crystalline salt | crystalline salt | crystalline salt |
| acetic acid | crystalline salt | crystalline salt | crystalline salt | crystalline salt | crystalline salt | crystalline salt |
| camphorsulfonic acid | oil | gum | gum | gum | gum | gum |
| ethanesulfonic acid | oil | oil | gum | gum | gum | oil |
| gentisic acid | oil | oil | gum | gum | gum | gum |
| hippuric acid | crystalline salt | gum | crystalline salt | crystalline salt | gum | crystalline salt (with free base) |
| methanesulfonic acid | oil | oil | gum | gum | gum | oil |
| oxalic acid | crystalline salt | crystalline salt | crystalline salt | crystalline salt | crystalline salt | crystalline salt |
| pamoic acid | counterion | counterion | counterion | counterion | counterion | counterion |
| salicylic acid | oil | gum | oil | gum | gum | gum |
| toluenesulfonic acid | oil | gum | gum | gum | gum | oil |
| l-ascorbic acid | gum | gum | gum | gum | gum | gum |
| malonic acid | gum | gum | gum | gum | gum | gum |
| glutaric acid | gum | gum | gum | gum | gum | gum |
| adipic acid | gum | gum | gum | gum | gum | gum |
| ethane-1,2-disulfonic acid | gum | gum | gum | gum | gum | gum |
| naphthalene-1,5-disulfonic acid | crystalline salt | crystalline salt | gum | crystalline salt | crystalline salt | gum |
| phthalic acid | gum | gum | gum | gum | gum | oil |

The acids found to form crystalline forms with S-oxprenolol were:

phosphoric acid;
1-hydroxy-2-naphthoic acid;
hippuric acid;
oxalic acid;
acetic acid; and
naphthalene-1,5-disulfonic acid.

Salt formation with these six acids was further evaluated.

Example 3—Further Salt Development

Phosphoric Acid

The phosphate salt was produced as follows. 2 mL of ethanol was added to ca. 500 mg of S-oxprenolol in a 20 mL screw cap vial to dissolve. 1.05 equivalents of phosphoric acid was added to the free base solution as a stock in 4 mL of ethanol. The pink solution was allowed to evaporate at ambient temperature (ca. 20° C.) and pressure. After ca. 10 days 100 μL of hexane was added. The preparation was dried under vacuum at ambient temperature (ca. 20° C.) for ca. 26 h. 6 mL of ethanol was added and partial dissolution was observed. Precipitation was observed immediately after the partial dissolution, which produced an immobile slurry. XRPD analysis was carried out on the solids.

200 μL of ethanol was added to a small amount of solids and stirred at ambient temperature (ca. 20° C.) for ca. 30 minutes to assess if ethanol addition would result in dissolution. 2 mL of ethanol was added to the immobile slurry to create a mobile slurry. The 200 μL slurry was also added. The slurry was isolated by Büchner filtration with Grade 1 filter paper and dried under vacuum at ambient temperature (ca. 20° C.) for ca. 22 h. The dried solids were analyzed by XRPD.

The salt was identified to be a mono-salt of phosphoric acid, and in particular S-oxprenolol dihydrogenphosphate.

The crystalline form of the salt with S-oxprenolol (S-oxprenolol dihydrogen-phosphate) formed during the initial salt screen was designated as Pattern 1, the XRPD characteristics of which are shown in Table 4 below and in FIG. 1.

TABLE 4

XRPD peak list for phosphate Pattern 1

| No. | Pos. [°2θ] | Height [cts] | FWHM Left [°2θ] | d-spacing [Å] | Rel. Int. [%] |
|---|---|---|---|---|---|
| 1 | 4.5646 | 5636.79 | 0.0640 | 19.3591 | 48.89 |
| 2 | 9.1617 | 1097.52 | 0.0768 | 9.6529 | 9.52 |
| 3 | 9.8570 | 73.27 | 0.1535 | 8.9735 | 0.64 |
| 4 | 10.9713 | 11530.18 | 0.0768 | 8.0645 | 100.00 |
| 5 | 12.1601 | 1190.88 | 0.0768 | 7.2786 | 10.33 |
| 6 | 13.7889 | 1751.78 | 0.0640 | 6.4223 | 15.19 |
| 7 | 13.8919 | 1085.21 | 0.0640 | 6.3749 | 9.41 |
| 8 | 14.7622 | 872.87 | 0.0895 | 6.0010 | 7.57 |
| 9 | 15.9375 | 854.46 | 0.0895 | 5.5610 | 7.41 |
| 10 | 16.5950 | 360.52 | 0.0512 | 5.3421 | 3.13 |
| 11 | 17.1022 | 2104.69 | 0.0895 | 5.1848 | 18.25 |
| 12 | 18.4045 | 2603.47 | 0.1151 | 4.8208 | 22.58 |
| 13 | 19.7827 | 1091.55 | 0.1023 | 4.4879 | 9.47 |
| 14 | 20.1141 | 1214.05 | 0.0768 | 4.4147 | 10.53 |
| 15 | 20.2525 | 1274.78 | 0.0768 | 4.3849 | 11.06 |
| 16 | 20.6485 | 5366.85 | 0.1151 | 4.3017 | 46.55 |
| 17 | 20.8870 | 829.91 | 0.0895 | 4.2531 | 7.20 |
| 18 | 21.2117 | 617.09 | 0.0384 | 4.1887 | 5.35 |
| 19 | 21.8018 | 1737.59 | 0.1279 | 4.0766 | 15.07 |
| 20 | 22.8514 | 2168.35 | 0.0895 | 3.8917 | 18.81 |
| 21 | 23.0481 | 1409.03 | 0.0768 | 3.8589 | 12.22 |
| 22 | 23.2448 | 839.57 | 0.1023 | 3.8267 | 7.28 |
| 23 | 23.6485 | 982.49 | 0.0512 | 3.7623 | 8.52 |
| 24 | 24.3565 | 763.77 | 0.0768 | 3.6545 | 6.62 |

TABLE 4-continued

XRPD peak list for phosphate Pattern 1

| No. | Pos. [°2θ] | Height [cts] | FWHM Left [°2θ] | d-spacing [Å] | Rel. Int. [%] |
|---|---|---|---|---|---|
| 25 | 24.7767 | 291.20 | 0.1279 | 3.5935 | 2.53 |
| 26 | 25.3354 | 893.48 | 0.1407 | 3.5155 | 7.75 |
| 27 | 25.7375 | 397.13 | 0.1279 | 3.4615 | 3.44 |
| 28 | 26.2775 | 1874.19 | 0.1407 | 3.3916 | 16.25 |
| 29 | 26.5963 | 245.53 | 0.0768 | 3.3516 | 2.13 |
| 30 | 27.1328 | 253.92 | 0.0895 | 3.2866 | 2.20 |
| 31 | 27.4473 | 206.04 | 0.0768 | 3.2496 | 1.79 |
| 32 | 27.7961 | 301.12 | 0.0768 | 3.2096 | 2.61 |
| 33 | 27.9890 | 241.58 | 0.1023 | 3.1878 | 2.10 |
| 34 | 29.3104 | 429.71 | 0.0512 | 3.0472 | 3.73 |
| 35 | 29.8260 | 170.76 | 0.1279 | 2.9957 | 1.48 |
| 36 | 30.3820 | 211.89 | 0.1535 | 2.9421 | 1.84 |
| 37 | 31.1133 | 155.01 | 0.1023 | 2.8746 | 1.34 |
| 38 | 31.9194 | 175.92 | 0.1023 | 2.8038 | 1.53 |
| 39 | 32.2274 | 217.56 | 0.1535 | 2.7777 | 1.89 |
| 40 | 32.5489 | 178.14 | 0.0768 | 2.7510 | 1.55 |
| 41 | 33.4381 | 208.84 | 0.1279 | 2.6799 | 1.81 |
| 42 | 33.7756 | 124.73 | 0.1279 | 2.6538 | 1.08 |
| 43 | 34.1255 | 234.26 | 0.1023 | 2.6274 | 2.03 |
| 44 | 34.6304 | 287.21 | 0.0768 | 2.5903 | 2.49 |

XRPD analysis of dihydrogen-phosphate Pattern 1 after heating to 40° C., drying at ambient temperature (ca. 20° C.) under vacuum and storage at 40° C./75% RH showed dihydrogenphosphate Pattern 1 to remain.

Further analysis of dihydrogenphosphate Pattern 1 from ethanol gave the following results.

Thermal analysis showed a mass loss of 0.6% up to ca. 104° C. A further loss of 1.0% was observed during the thermal event. The weight losses corresponded to 0.3 equivalents of water.

1H NMR analysis showed no ethanol and the material to be consistent with the structure.

PLM analysis showed birefringent particles with a rod-like morphology.

HPLC analysis indicated 99.4% area purity. The input purity was 99.9% Area.

1-Hydroxy-2-naphthoic Acid (Xinafoic Acid)

Xinafoate Pattern 1 was observed from experiments from ethanol, ethyl acetate, t-BME, THF and water. XRPD analysis of xinafoate Pattern 1 after drying at 40° C. under vacuum and storage at 40° C./75% RH showed xinafoate Pattern 1 was retained.

Thermal analysis of xinafoate Pattern 1 from t-BME showed the material to be anhydrous. DSC analysis showed an endothermic event with onset ca. 78° C. (peak at 85° C.).

The xinafoate had a relatively low melting point.

Hippuric Acid (N-benzoylglycine)

Hippurate Pattern 1 was observed from experiments from acetone, ethyl acetate and t-BME. XRPD analysis of hippurate Pattern 1 after drying at 40° C. under vacuum showed hippurate Pattern 1 was retained. Upon storage at 40° C./75% RH deliquescence was observed to amorphous materials.

The hippurate salt showed poor hygroscopicity properties.

Oxalic Acid

The salt formation experiments with oxalic acid returned two crystalline potential salts. The following results were obtained. The salt was determined to be the a mono-oxalate salt.

Oxalate Pattern 1: Oxalate Pattern 1 was observed from experiments from acetone, ethyl acetate, t-BME and THF. XRPD analysis of oxalate Pattern 1 after drying at 40° C.

under vacuum and storage at 40° C./75% RH showed oxalate Pattern 1 was retained.

Further analysis of oxalate Pattern 1 from THE gave the following results:

Thermal analysis (FIG. 31) showed the material to be anhydrous with the onset of degradation observed above ca. 175° C. DSC analysis showed an endothermic event with onset ca. 128° C. (peak at 130° C.).

1H NMR analysis (FIG. 32) showed no THF and the material to be consistent with the structure.

Further analysis of oxalate Pattern 1 from ethyl acetate gave the following results:

PLM analysis showed birefringent particles with no clearly defined morphology.

Aqueous solubility was observed to be 32 mg/mL.

Oxalate Pattern 1 & 2: Oxalate Pattern 2 was observed from ethanol and water. XRPD analysis of oxalate Pattern 2 after drying at 40° C. under vacuum showed a mixture of Pattern 1 and 2 was obtained. After storage at 40° C./75% RH the mixture was observed to be predominantly unchanged.

Further analysis of the oxalate Pattern 1 & 2 mixture from ethanol gave the following results:

Thermal analysis showed weight losses of 1.3% and 0.7% up to ca. 150° C. The weight losses observed corresponded to 0.4 equivalents of water. DSC analysis showed two endothermic events with onsets ca. 51° C. (peak at 81° C.) and 110° C. (peak at 127° C.). A shoulder peak was observed ca. 113° C.

1H NMR analysis showed no ethanol and the material to be consistent with the structure.

Figure 2:
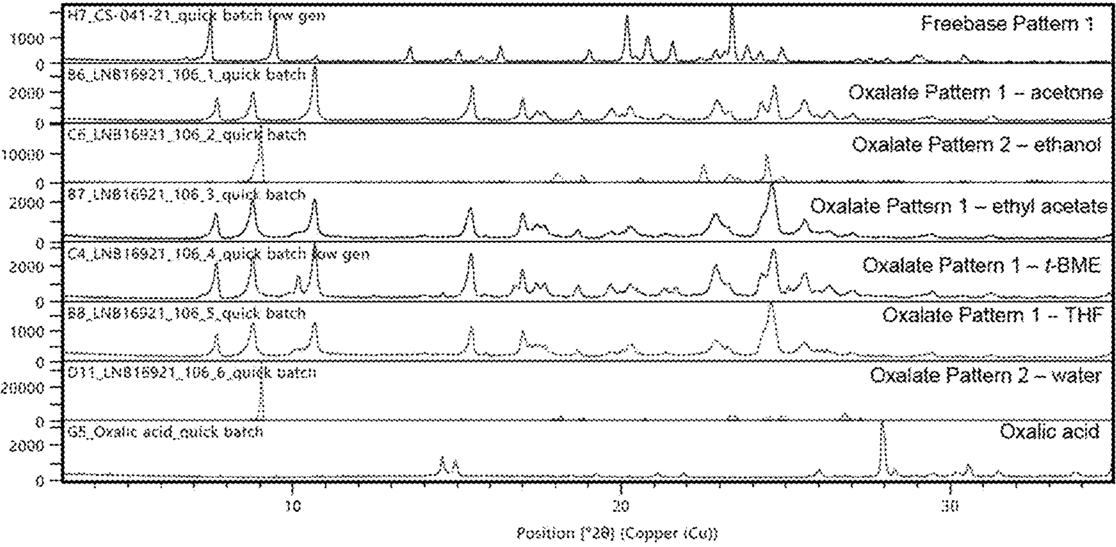
FIG. 2 shows XRPD diffractograms of S-oxprenolol free base, S-oxprenolol oxalate Patterns 1 and 2, and oxalic acid.

XRPD diffractograms of oxalate Patterns 1 and 2 are given in FIG. 2.

Acetic Acid

The salt formation experiments with acetic acid returned two polymorphs of the potential salt. The following results were obtained.

Acetate Pattern 1 was observed from all 6 solvent systems. XRPD analysis of acetate Pattern 1 from ethanol and water after drying at 40° C. under vacuum showed acetate Pattern 1 was retained. Pattern 1 from ethanol was observed to remain after storage at 40° C./75% RH but partially deliquesced. Pattern 1 from water was observed to remain after storage at 40° C./75% RH. XRPD analysis of acetate Pattern 1 from acetone, ethyl acetate, t-BME and THE after drying at 40° C. under vacuum showed Pattern 2 was obtained.

Pattern 2 from acetone, ethyl acetate and t-BME were observed to have deliquesced after storage at 40° C./75% RH. Predominantly amorphous material was obtained from ethyl acetate and t-BME after storage at 40° C./75% RH. The Pattern 2 material from acetone after drying at 40° C. under vacuum showed preferred orientation and Pattern 2 peaks remained after storage at 40° C./75% RH. The Pattern 2 material from THF was observed to partially deliquesce after storage at 40° C./75% RH but still showed some Pattern 2 peaks. Thermal analysis of Acetate Pattern 2 showed the material to be anhydrous. An endothermic event was observed ca. 60° C. (peak at 101° C.).

The acetate salt showed poor hygroscopicity properties.

Naphthalene-1,5-disulfonic Acid

The naphthalene-1,5-disulfonic acid experiments returned two crystalline potential salts from evaporation from the anti-solvent addition experiments. Pattern 2 was only observed as a mixture with Pattern 1 from t-BME. The additional peaks ca. 9.9, 11.6, 13.9, 16.7 and 16.9 ° 2θ were observed for diffractogram obtained from the t-BME experiment. The following results were obtained:

Naphthalene-1,5-disulfonate Pattern 1 was observed from experiments from acetone, ethanol and THF.

The naphthalene-1,5-disulfonic acid material from acetone was observed to be solids and the material from ethanol, t-BME and THF was observed to be sticky solids.

XRPD analysis of naphthalene-1,5-disulfonate Pattern 1 after drying at 40° C. under vacuum showed that Pattern 1 was retained.

Analysis of naphthalene-1,5-disulfonate Pattern 1 from acetone following anti-solvent addition gave the following results:

Initial thermal analysis prior to drying under vacuum showed a loss of 3.9% up to ca. 200° C. The loss observed corresponded to 0.4 equivalents of acetone. DSC analysis showed a broad endothermic event with onset ca. 28° C. (peak at 94° C.).

Thermal analysis after drying under vacuum at 40° C. showed a loss of 3.3% up to ca. 100° C. The loss observed corresponded to 0.3 equivalents of acetone. DSC analysis showed a broad endothermic event with peak ca. 100° C. The onset temperature was not able to be determined.

Conclusion of Further Salt Development

Six crystalline salts were produced during the initial salt screen. These salts were formed with phosphoric acid, 1-hydroxy-2-naphthoic acid, hippuric acid, oxalic acid, acetic acid and naphthalene-1,5-disulfonic acid.

The formation and physical properties of these six salts were further investigated.

It was found that the salt formed with phosphoric acid (S-oxprenolol dihydrogenphosphate) was suited for use in pharmaceutical formulations. In particular, S-oxprenolol dihydrogenphosphate had a high melting point and good crystallinity.

The oxalate salt also had favourable physical properties. However, oxalate does not have a favourable toxicity profile and this salt is less well-suited to pharmaceutical formulation.

The remaining crystalline salts were not as well suited to pharmaceutical formulation. The xinafoate and naphthalene-1,5-disulfonate have large molecular weights which were not justified by any changes in physical properties. The hippurate and acetate salts showed poor hygroscopicity properties.

Example 4—Dihydrogenphosphate Polymorph Screen

Amorphous S-oxprenolol dihydrogenphosphate was produced by lyophilisation of the salt from water.

A solvent solubility screen was carried out to gain an understanding of the solubility and assist in the selection of appropriate solvent systems for the polymorph screen. The results of the approximate solubility screen of amorphous S-oxprenolol dihydrogenphosphate salt are presented in Table 5 (with Pattern 2, Pattern 3 or a mixture of Patterns 2 and 3 indicated) and summarized below.

High solubility >194 mg/mL was observed for 50% acetone: 50% water (% v/v), DMSO, methanol, DMF and water.

Moderate solubility of ≥47 mg/mL was observed for 90% 2-propanol: 10% water (% v/v), DMA and NMP.

Low solubility <10 mg/mL was observed for 24 of the 32 solvent systems tested.

XRPD analysis showed predominantly phosphate Pattern 2 or 3 was obtained and mixtures of Pattern 2 and 3 were observed.

TABLE 5

Solvent solubility screen results

| Solvent | Solubility (mg/mL) | XRPD Analysis |
|---|---|---|
| 1,4-Dioxane | <10 | 2 + 3 |
| 1-Butanol | <10 | 2 + 3 |
| 1-Propanol | <10 | 2 |
| 2-Methyl THF | <10 | 2 + 3 |
| 2-Propanol | <10 | 3 |
| 90% 2-Propanol:10% Water (% v/v) (calculated $a_w$ 0.6) | 47 | oil |
| 2-Methyl-1-Propanol | <9 | 2 |
| Acetone | <10 | 3 |
| 50% Acetone:50% Water (% v/v) (calculated $a_w$ 0.9) | >201# | 3 |
| Acetonitrile | <9 | 2 |
| Anisole | <9 | 2 |
| Benzyl Alcohol | <10 | 2 |
| Butyl Acetate | <10 | 2 |
| Dichloromethane | <10 | gum |
| Diisopropyl Ether | <10 | 2 |
| Dimethylsulfoxide | >205# | solution |
| Ethanol | <10 | 2 + 3 |
| 98.5% Ethanol:1.5% Water (% v/v) (calculated $a_w$ 0.2) | <9 | gum |
| Ethyl Acetate | <10 | 2 + 3 |
| n-Heptane | <10 | 3 |
| n-Hexane | <10 | 3 |
| Isopropyl Acetate | <10 | 2 |
| Methanol | >195# | 3 |
| Methylethyl Ketone | <10 | 2 |
| Methylisobutyl Ketone | <10 | 3 |
| N,N-Dimethylacetamide | 67# | solution |
| N,N-Dimethylformamide | >194# | solution |
| N-Methylpyrrolidone | 74# | solution |
| tert-Butylmethyl Ether | <10 | 3 |
| Tetrahydrofuran | <9 | 3 |
| Toluene | <10 | 3 |
| Water | >208 | gum |

Patterns 2 and 3 were characterised by XRPD and the results are shown in Tables 6 and 7 below.

TABLE 6

XRPD peak list for phosphate Pattern 2

| No. | Pos. [°2θ] | Height [cts] | FWHM Left [°2θ] | d-spacing [Å] | Rel. Int. [%] |
|---|---|---|---|---|---|
| 1 | 3.9492 | 558.92 | 0.0512 | 22.3740 | 8.39 |
| 2 | 4.1342 | 957.05 | 0.0640 | 21.3737 | 14.37 |
| 3 | 4.3912 | 3496.72 | 0.0640 | 20.1231 | 52.49 |
| 4 | 4.7581 | 143.50 | 0.0768 | 18.5722 | 2.15 |
| 5 | 6.8382 | 6491.81 | 0.0768 | 12.9266 | 97.44 |
| 6 | 7.8246 | 2331.74 | 0.0768 | 11.2992 | 35.00 |
| 7 | 8.7963 | 214.14 | 0.0768 | 10.0531 | 3.21 |
| 8 | 9.2367 | 225.33 | 0.0768 | 9.5747 | 3.38 |
| 9 | 11.4074 | 162.34 | 0.1023 | 7.7571 | 2.44 |
| 10 | 12.0325 | 169.08 | 0.0768 | 7.3556 | 2.54 |
| 11 | 12.9431 | 1400.31 | 0.0895 | 6.8400 | 21.02 |
| 12 | 13.2067 | 230.77 | 0.0640 | 6.7041 | 3.46 |
| 13 | 13.6773 | 914.26 | 0.1023 | 6.4745 | 13.72 |
| 14 | 14.2577 | 156.56 | 0.0768 | 6.2122 | 2.35 |
| 15 | 14.5714 | 540.01 | 0.0895 | 6.0792 | 8.11 |
| 16 | 15.6735 | 269.29 | 0.0512 | 5.6541 | 4.04 |
| 17 | 17.0147 | 1533.19 | 0.0768 | 5.2113 | 23.01 |
| 18 | 17.1696 | 1407.82 | 0.0895 | 5.1646 | 21.13 |
| 19 | 17.7254 | 608.35 | 0.1151 | 5.0039 | 9.13 |
| 20 | 18.4098 | 290.53 | 0.0768 | 4.8194 | 4.36 |
| 21 | 19.3198 | 1331.05 | 0.1279 | 4.5944 | 19.98 |
| 22 | 20.1748 | 190.48 | 0.0512 | 4.4016 | 2.86 |
| 23 | 20.4270 | 294.97 | 0.0768 | 4.3478 | 4.43 |
| 24 | 20.6275 | 305.65 | 0.0768 | 4.3060 | 4.59 |
| 25 | 20.9324 | 269.37 | 0.0640 | 4.2439 | 4.04 |
| 26 | 21.4537 | 258.10 | 0.1023 | 4.1420 | 3.87 |
| 27 | 21.9418 | 739.65 | 0.1023 | 4.0510 | 11.10 |
| 28 | 22.5140 | 6662.29 | 0.0895 | 3.9493 | 100.00 |
| 29 | 22.6320 | 5304.77 | 0.0895 | 3.9289 | 79.62 |
| 30 | 22.9419 | 1584.83 | 0.1151 | 3.8766 | 23.79 |
| 31 | 23.4594 | 6402.35 | 0.1404 | 3.7891 | 96.10 |
| 32 | 23.5552 | 4076.15 | 0.1092 | 3.7833 | 61.18 |
| 33 | 23.8152 | 369.39 | 0.1248 | 3.7333 | 5.54 |
| 34 | 24.2056 | 1550.91 | 0.1248 | 3.6739 | 23.28 |
| 35 | 25.0951 | 1419.36 | 0.1872 | 3.5457 | 21.30 |
| 36 | 26.0406 | 242.78 | 0.2184 | 3.4190 | 3.64 |
| 37 | 26.4366 | 486.73 | 0.0468 | 3.3687 | 7.31 |
| 38 | 26.5218 | 487.75 | 0.0624 | 3.3581 | 7.32 |
| 39 | 26.9126 | 569.93 | 0.0624 | 3.3102 | 8.55 |
| 40 | 26.9463 | 555.22 | 0.0468 | 3.3144 | 8.33 |
| 41 | 27.4452 | 425.61 | 0.1560 | 3.2472 | 6.39 |
| 42 | 28.0698 | 90.33 | 0.1872 | 3.1763 | 1.36 |
| 43 | 28.7868 | 200.76 | 0.1560 | 3.0988 | 3.01 |
| 44 | 29.3127 | 62.33 | 0.1560 | 3.0444 | 0.94 |
| 45 | 30.0591 | 291.33 | 0.0936 | 2.9705 | 4.37 |
| 46 | 30.6419 | 97.44 | 0.1560 | 2.9153 | 1.46 |
| 47 | 31.7531 | 49.15 | 0.2496 | 2.8158 | 0.74 |
| 48 | 32.6990 | 12.46 | 0.7488 | 2.7365 | 0.19 |
| 49 | 34.1210 | 82.58 | 0.1092 | 2.6256 | 1.24 |
| 50 | 34.3476 | 147.43 | 0.0936 | 2.6088 | 2.21 |
| 51 | 34.7467 | 501.72 | 0.2184 | 2.5797 | 7.53 |

TABLE 7

XRPD peak list for phosphate Pattern 3

| No. | Pos. [°2θ] | Height [cts] | FWHM Left [°2θ] | d-spacing [Å] | Rel. Int. [%] |
|---|---|---|---|---|---|
| 1 | 4.7712 | 4565.33 | 0.0768 | 18.5213 | 100.00 |
| 2 | 7.0817 | 2264.49 | 0.0768 | 12.4827 | 49.60 |
| 3 | 7.1743 | 953.91 | 0.0384 | 12.3219 | 20.89 |
| 4 | 8.2092 | 1309.57 | 0.1023 | 10.7707 | 28.69 |
| 5 | 9.5747 | 543.16 | 0.1151 | 9.2375 | 11.90 |
| 6 | 9.8260 | 111.54 | 0.0768 | 9.0018 | 2.44 |
| 7 | 11.2226 | 157.24 | 0.1023 | 7.8845 | 3.44 |
| 8 | 11.5751 | 590.23 | 0.0768 | 7.6451 | 12.93 |
| 9 | 13.0309 | 403.94 | 0.1023 | 6.7941 | 8.85 |
| 10 | 13.3717 | 532.45 | 0.0640 | 6.6217 | 11.66 |
| 11 | 13.7278 | 327.99 | 0.0512 | 6.4507 | 7.18 |
| 12 | 14.1970 | 813.05 | 0.0895 | 6.2386 | 17.81 |
| 13 | 14.3616 | 738.83 | 0.0895 | 6.1675 | 16.18 |
| 14 | 15.1783 | 223.29 | 0.1023 | 5.8374 | 4.89 |
| 15 | 15.8220 | 282.77 | 0.1535 | 5.6013 | 6.19 |
| 16 | 16.6164 | 250.61 | 0.0768 | 5.3353 | 5.49 |
| 17 | 17.7384 | 426.30 | 0.1151 | 5.0003 | 9.34 |
| 18 | 17.9565 | 565.89 | 0.0512 | 4.9400 | 12.40 |
| 19 | 18.2498 | 353.14 | 0.1535 | 4.8613 | 7.74 |
| 20 | 18.8583 | 414.51 | 0.0512 | 4.7058 | 9.08 |
| 21 | 19.2368 | 387.50 | 0.1279 | 4.6140 | 8.49 |
| 22 | 19.6705 | 211.35 | 0.1535 | 4.5133 | 4.63 |
| 23 | 20.3285 | 202.32 | 0.2047 | 4.3686 | 4.43 |
| 24 | 20.8835 | 536.86 | 0.1279 | 4.2538 | 11.76 |
| 25 | 21.5879 | 604.43 | 0.1023 | 4.1165 | 13.24 |
| 26 | 22.5134 | 1423.35 | 0.1151 | 3.9494 | 31.18 |
| 27 | 22.7326 | 2458.77 | 0.1023 | 3.9118 | 53.86 |
| 28 | 23.2165 | 1437.96 | 0.2047 | 3.8313 | 31.50 |
| 29 | 23.4757 | 1567.80 | 0.1279 | 3.7896 | 34.34 |
| 30 | 23.7686 | 813.42 | 0.1023 | 3.7436 | 17.82 |
| 31 | 24.0175 | 717.17 | 0.1279 | 3.7053 | 15.71 |
| 32 | 24.7349 | 401.74 | 0.1279 | 3.5995 | 8.80 |
| 33 | 25.0092 | 569.74 | 0.1535 | 3.5606 | 12.48 |
| 34 | 25.7737 | 473.26 | 0.0895 | 3.4567 | 10.37 |
| 35 | 26.2870 | 344.87 | 0.1023 | 3.3904 | 7.55 |

TABLE 7-continued

XRPD peak list for phosphate Pattern 3

| No. | Pos. [°2θ] | Height [cts] | FWHM Left [°2θ] | d-spacing [Å] | Rel. Int. [%] |
|---|---|---|---|---|---|
| 36 | 26.9511 | 499.18 | 0.2558 | 3.3083 | 10.93 |
| 37 | 27.3771 | 279.15 | 0.1023 | 3.2578 | 6.11 |
| 38 | 28.3332 | 157.05 | 0.2303 | 3.1500 | 3.44 |
| 39 | 29.0826 | 84.57 | 0.2558 | 3.0705 | 1.85 |
| 40 | 29.8417 | 129.08 | 0.1535 | 2.9941 | 2.83 |
| 41 | 30.4075 | 85.49 | 0.2047 | 2.9397 | 1.87 |
| 42 | 32.2081 | 70.98 | 0.2558 | 2.7793 | 1.55 |
| 43 | 33.9692 | 36.58 | 0.1535 | 2.6392 | 0.80 |

The XRPD diffractograms of S-oxprenolol dihydrogenphosphate Pattern 2 and Pattern 3 are shown in FIGS. 3 and 4 respectively.

A further sample of Pattern 3 was prepared as follows:

To ca. 2.5 g of S-oxprenolol in a 100 mL Duran flask, 10 mL of ethanol was added to dissolve.

1.05 equivalents of phosphoric acid was added to the freebase solution as a 0.5 M stock in 20 mL of ethanol.

30 mL of heptane was stirred at ambient (ca. 20° C.) in a 250 mL Duran flask and the S-oxprenolol/phosphoric acid solution was added dropwise over ca. 9 minutes.

An off-white precipitate was observed.

Ca. 0.5 mL of the slurry was isolated by centrifuge filtration (nylon, 0.22 μm) and analyzed by XRPD.

The slurry was isolated by Büchner filtration with Grade 1 filter paper and dried under vacuum at ambient temperature (ca. 20° C.) for ca. 69 h.

The isolated yield was 2.97 g, 87%.

XRPD analysis showed phosphate Pattern 2 was obtained prior to drying and phosphate Pattern 3 was obtained after drying.

Thermal analysis showed a loss of 2.1% up to ca. 100° C. followed by a loss of 0.1% up to ca. 120° C. The weight losses observed corresponded to 0.5 equivalents of water. DSC analysis showed an endothermic event with onset ca. 88° C. (peak at 91° C.) followed by a shallow endothermic event with onset ca. 171° C. (peak at 172° C.).

$^{1}$H NMR analysis showed 0.1 equivalents of ethanol.

$^{31}$P NMR analysis with 1.0 equivalents of triphenyl phosphate showed the salt to be a mono-phosphate salt.

Phosphate Pattern 2 was isolated from temperature cycling in 1-butanol. XRPD analysis after drying showed the solids had converted to phosphate Pattern 3.

Conclusion

S-oxprenolol dihydrogenphosphate Pattern 3 was identified as the most suitable polymorph for scale up. Pattern 3 shows good crystallinity with a rod-like morphology, has a high melting point and is stable.

Example 4—Comparison of Dihydrogenphosphate Polymorphs

S-oxprenolol dihydrogenphosphate Pattern 3 was found to have improved suitability for scale up compared with Pattern 1 and Pattern 2. In particular, Pattern 3 was found to have improved stability compared with Pattern 1 and Pattern 2.

S-oxprenolol dihydrogenphosphate Pattern 3 was observed to show excellent stability after 7 days storage at ambient temperature and after 7 days storage at 40° C./75% RH, in each case with an HPLC purity of >99.9% area achieved following storage.

In contrast, Pattern 1 and Pattern 2 of S-oxprenolol dihydrogenphosphate were found to have issues with stability and ability to scale up.

Example 5—Single Crystal Analysis

Single Crystal X-ray Analysis (SXRD)

Suitable crystals of S-oxprenolol dihydrogenphosphate Pattern 2 and Pattern 3 were selected and mounted in a loop using paratone oil. Data were collected using a Bruker D8Venture diffractometer equipped with a Photon III detector operating in shutterless mode at 100 K with Cu-Kα radiation (1.54178 Å). All non-hydrogen atoms were located in the Fourier map and their positions refined prior to describing the thermal movement of all non-hydrogen atoms anisotropically.

The structure was solved in the Olex2 software package with the SheIXT (intrinsic phasing) structure solution program and refined with the SheIXL refinement package using Least Squares minimisation. Data were collected, solved, and refined in the chiral orthorhombic space group $P2_12_12_1$ for Pattern 2 and in the chiral monoclinic space group $P2_1$ for Pattern 3. A series of restraints were applied to the final refinement. All CH, $CH_2$ and $NH_2$ groups were refined with fixed Uiso of 1.2 times. All $CH_3$, OH and $OH_2$ groups were refined with fixed Uiso of 1.5 times.

S-oxprenolol Dihydrogenphosphate Pattern 2

Single crystals of S-oxprenolol dihydrogenphosphate Pattern 2 were grown by rapid cooling of an ethanol solution of S-oxprenolol dihydrogenphosphate from ambient temperature to 4° C.

The unit cell dimensions of the collected structure were as follows:

Orthorhombic $P2_12_12_1$
a=7.7822(4) Å α=90°
b=13.2653(5) Å β=90° C.
c=39.5732(15) Å γ=90°
Volume=4085.3 (3) $Å^3$
Z=4, Z`=2
Temperature=100 (2) K The asymmetric unit was comprised of two formula units of S-oxprenolol dihydrogenphosphate, and one ethanol molecule (i.e. a hemi-ethanol solvate).

The final refinement parameters were as follows:

$R_1[I>2\sigma(I)]$=2.80%
GooF (Goodness of fit)=1.039
$wR_2$ (all data)=7.76%
$R_{int}$=5.69%
Flack×parameter=0.012(4)

S-oxprenolol dihydrogenphosphate Pattern 3

Single crystals of S-oxprenolol dihydrogenphosphate Pattern 3 were obtained by addition of THE anti-solvent into a 90% acetone: 10% water solution and storing at ambient conditions for about two weeks.

The unit cell dimensions of the collected structure were as follows:

Orthorhombic $P2_1$
a=7.76070(10) Å α=90°
b=36.7729(6) Å β=94.0602 (11)° C.
c=12.9496(2) Å γ=90°
Volume=3686.33(10) $Å^3$
Z=8, Z`=4
Temperature=100 K The asymmetric unit was comprised of four formula units of S-oxprenolol dihydrogenphosphate, and one water molecule (i.e. 0.25 water molecules per S-oxprenolol dihydrogenphosphate molecule).

The final refinement parameters were as follows:

$R_1[I>2\sigma(I)]=3.09\%$

GooF (Goodness of fit)=1.038

$wR_2$ (all data)=8.10%

$R_{int}=5.42\%$

Flack×parameter=0.000(6)

The invention claimed is:

1. A pharmaceutically acceptable acid addition salt of:

(i) S-oxprenolol; and (ii) phosphoric acid, wherein the pharmaceutically acceptable acid addition salt is S-oxprenolol dihydrogenphosphate.

2. A pharmaceutically acceptable acid addition salt according to claim 1, wherein the pharmaceutically acceptable acid addition salt is crystalline.

3. A pharmaceutically acceptable acid addition salt according to claim 1, wherein the pharmaceutically acceptable acid addition salt is S-oxprenolol dihydrogenphosphate.

4. A pharmaceutically acceptable acid addition salt according to claim 1, wherein the S-oxprenolol dihydrogenphosphate is in the form of S-oxprenolol dihydrogenphosphate crystalline polymorph Pattern 3 having an x-ray powder diffraction pattern comprising peaks at 4.8°, 7.1° and 8.2°±0.2° 2θ.

5. A pharmaceutically acceptable acid addition salt according to claim 4, wherein the x-ray powder diffraction pattern further comprises peaks at 22.5°, 22.7° and 23.2°±0.2° 2θ.

6. A pharmaceutically acceptable acid addition salt according to claim 4, wherein the x-ray powder diffraction pattern comprises seven or more peaks selected from 4.8°, 7.1°, 8.2°, 14.2°, 14.4°, 22.5°, 22.7°, 23.2°, 23.5° and 23.8°±0.2° 2θ.

7. A composition comprising at least 60 wt % of a pharmaceutically acceptable acid addition salt as defined in claim 1 relative to the total weight of the composition.

8. A composition according to claim 7, wherein the composition comprises no more than 30 wt % of R-oxprenolol or a salt thereof relative to the total weight of the composition.

9. A pharmaceutical composition comprising (i) a pharmaceutically acceptable acid addition salt as defined in claim 1 and (ii) a pharmaceutically acceptable excipient, carrier or diluent.

10. A pharmaceutical composition according to claim 9, wherein the enantiomeric excess of the pharmaceutically acceptable acid addition salt in the pharmaceutical composition is at least 90%.

11. A pharmaceutical composition according to claim 9, wherein the enantiomeric excess of the pharmaceutically acceptable acid addition salt in the pharmaceutical composition is at least 95%.

12. A pharmaceutical composition according to claim 9, wherein the pharmaceutical composition is a tablet.

* * * * *